(12) United States Patent
O'Day et al.

(10) Patent No.: US 9,314,589 B2
(45) Date of Patent: Apr. 19, 2016

(54) METHOD OF TREATING AN INTRAVASCULAR SITE IN A PATIENT, AND THROMBOLYSIS CATHETER THEREFOR

(75) Inventors: Therese O'Day, Bloomington, IN (US); Frank J. Fisher, Bloomington, IN (US); Lindsay Koren, Bloomington, IN (US); Mark Allen Magnuson, Bloomington, IN (US); Richard Earl Luedemann, Ellettsville, IN (US); Shyam Kuppurathanam, Bloomington, IN (US); Keith R. Milner, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 523 days.

(21) Appl. No.: 13/695,915

(22) PCT Filed: May 3, 2011

(86) PCT No.: PCT/US2011/034953
§ 371 (c)(1),
(2), (4) Date: Nov. 2, 2012

(87) PCT Pub. No.: WO2011/140059
PCT Pub. Date: Nov. 10, 2011

(65) Prior Publication Data
US 2013/0046282 A1 Feb. 21, 2013

Related U.S. Application Data

(60) Provisional application No. 61/331,019, filed on May 4, 2010.

(51) Int. Cl.
*A61M 25/00* (2006.01)
(52) U.S. Cl.
CPC .................................. *A61M 25/007* (2013.01)

(58) Field of Classification Search
CPC ................. A61M 2025/0073; A61M 25/0009; A61M 25/0015; A61M 25/007
See application file for complete search history.

(56) References Cited

U.S. PATENT DOCUMENTS

| 4,784,638 A | 11/1988 | Ghajar et al. |
| 5,160,325 A | 11/1992 | Nichols et al. |
| 5,267,979 A | 12/1993 | Appling et al. |
| 5,425,723 A | 6/1995 | Wang |

(Continued)

FOREIGN PATENT DOCUMENTS

| EP | 0864336 | 9/1998 |
| EP | 2005049110 | 6/2005 |

(Continued)

OTHER PUBLICATIONS

Poulsen, Stephanie S., Mottola, Jim, Stoker, Ronald L., An In Vitro Comparison of Thrombolytic Infusion Catheters, article, 1998, 8 pages, Merit Medical Systems, Inc., South Jordan, Utah.

*Primary Examiner* — Imani Hayman
(74) *Attorney, Agent, or Firm* — Liell & McNeil

(57) ABSTRACT

A method of treating an intravascular site in a patient includes spraying jets of treatment fluid out of spray orifices formed in an elongate catheter body, and changing an impingement pattern of the treatment fluid on material within the intravascular site in response to a torque induced by a back pressure of the jets. A thrombolysis catheter includes an elongate catheter body having a plurality of spray orifices formed in a body wall, and communicating with a fluid lumen longitudinally extending in the elongate catheter body. The plurality of spray orifices define a torque inducing spray jet pattern, whereby a back pressure of spray jets exiting the spray orifices induces a torque on the elongate catheter body.

15 Claims, 6 Drawing Sheets

(56) References Cited

U.S. PATENT DOCUMENTS

| | | |
|---|---|---|
| 5,643,228 A | 7/1997 | Schucart et al. |
| 5,797,886 A | 8/1998 | Roth et al. |
| 5,957,901 A | 9/1999 | Mottola et al. |
| 6,063,069 A | 5/2000 | Cragg et al. |
| 6,117,125 A | 9/2000 | Rothbarth et al. |
| 6,246,914 B1 * | 6/2001 | de la Rama ............ A61N 1/06 604/523 |
| 6,669,679 B1 * | 12/2003 | Savage et al. ................ 604/500 |
| 6,852,097 B1 | 2/2005 | Fulton, III |
| 2006/0229573 A1 | 10/2006 | Lamborne |

FOREIGN PATENT DOCUMENTS

| | | |
|---|---|---|
| WO | 0151116 | 7/2001 |
| WO | 2005049110 | 6/2005 |

* cited by examiner

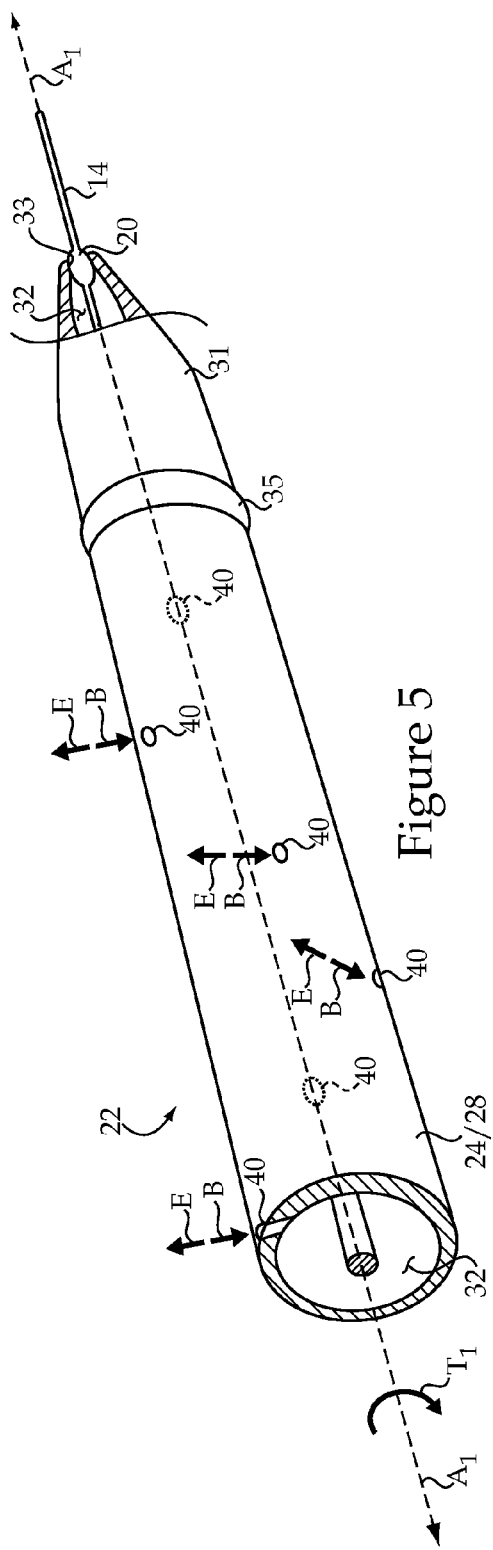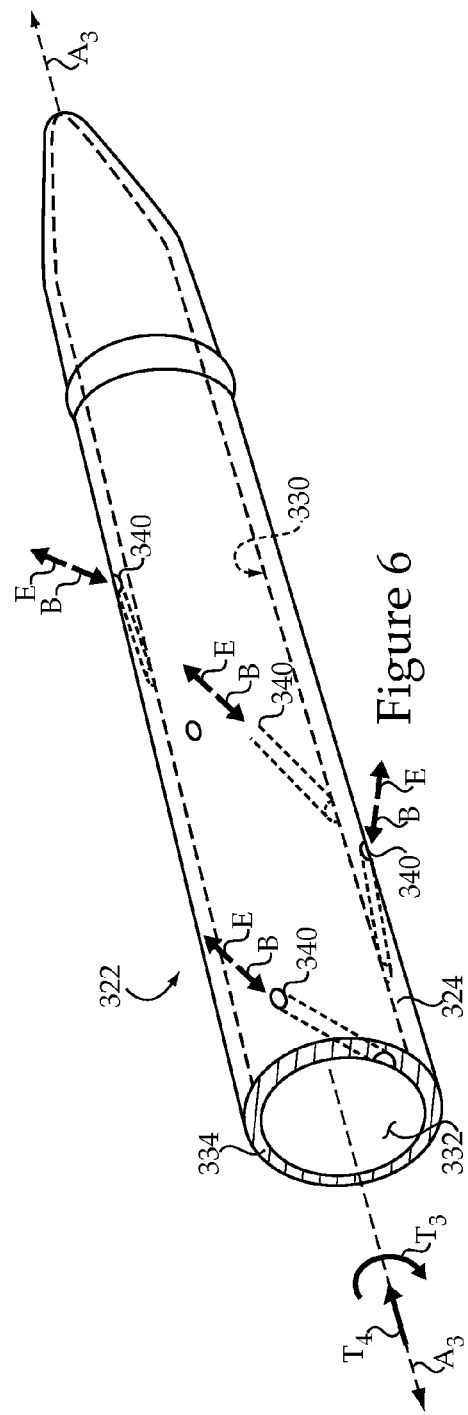

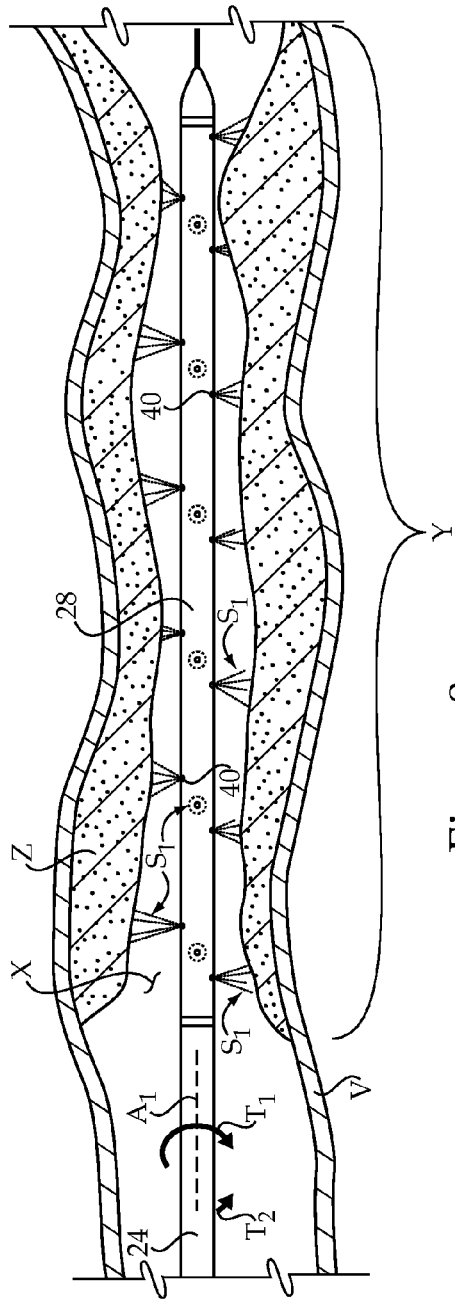
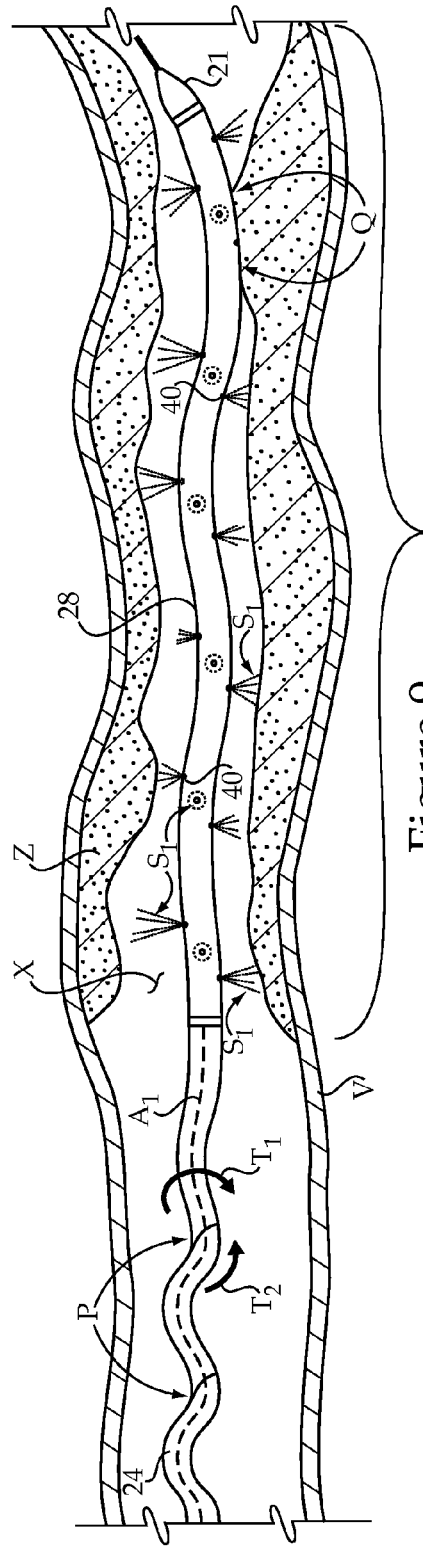
Figure 8
Figure 9

METHOD OF TREATING AN INTRAVASCULAR SITE IN A PATIENT, AND THROMBOLYSIS CATHETER THEREFOR

TECHNICAL FIELD

The present disclosure relates generally to techniques for treating intravascular sites in a patient, and relates more particularly to changing an impingement pattern of treatment fluid on material within an intravascular site by spraying jets of treatment fluid from an elongate catheter body.

BACKGROUND

Percutaneous access to the cardiovascular system is used to diagnose, evaluate, and treat a variety of conditions. A typical procedure involves passing a wire guide through an opening in a patient's skin which connects with a vascular structure such as a vein or artery. The wire guide can then be passed through the cardiovascular system to a location of interest within the patient. Once the wire guide has been appropriately positioned, a catheter can be passed into the patient and guided by the wire guide to a location where the procedure is to be performed. Angioplasty, imaging, and the placement of stents, grafts, filters and other devices, are common procedures which are performed according to variations of the above general technique. It is also common to use percutaneous access for the placement of catheters which deliver fluid at an intraluminal treatment site. Devices known as infusion catheters are commonly used to deliver a therapeutic treatment fluid such as a thrombolytic agent to a thrombus within a vein or artery.

A wide variety of infusion catheter designs are known and commercially available. A typical infusion procedure may involve leaving an infusion catheter within a patient for period of time while treatment fluid flows from a fluid supply into the infusion catheter, and thenceforth into an intraluminal space. In the case of dissolving a thrombus, known generally as "thrombolysis," thrombolytic agents effused from a catheter into an intravascular site chemically dissolve material of the thrombus. A variety of factors can influence how long a thrombolytic procedure lasts. Size of the vascular structure which includes the thrombus, the type of thrombolytic agent, geometry and/or age of the thrombus, and still other factors such as the distance fluid must travel from an extraluminal fluid supply to the treatment site, can all affect the selection and administration of a particular procedure.

A variety of thrombolytic agents are well known and widely used. It is generally desirable to avoid overusing thrombolytic agents, as such materials tend to be relatively expensive. If used in excess, thrombolytics can negatively affect parts of a patient's body outside of an intended treatment site, such as by causing bleeding. In response to these and other concerns, a variety of designs which use not only a thrombolytic agent but also some mechanical strategy to break up a thrombus have been proposed. Cutting implements, suction devices, systems using ultrasonic energy, and still others have found a certain degree of commercial success. These conventional strategies, however, tend to have a number of disadvantages. Among these is the common requirement of a power source to spin a catheter from outside a patient's body, generate ultrasonic energy, aspirate tissue, or for other purposes.

SUMMARY OF THE INVENTION

In one aspect, a method of treating an intravascular site in a patient includes supplying a treatment fluid to a fluid lumen of an elongate catheter body positioned within an intravascular site, and spraying jets of treatment fluid out of spray orifices formed in the elongate catheter body. The method further includes inducing a torque on the elongate catheter body by way of a back pressure of the jets, and changing an impingement pattern of the treatment fluid on material within the intravascular site in response to the torque.

In another aspect, a thrombolysis catheter includes an elongate catheter body having a supply segment and a spray segment, and defining a longitudinal axis extending through the supply segment and the spray segment. The elongate catheter body further includes an outer surface, an inner surface defining a longitudinally extending fluid lumen, and a body wall extending between the inner surface and the outer surface. The elongate catheter body further defines a fluid supply port located in the supply segment and connecting with the fluid lumen, and a plurality of spray orifices formed in the body wall within the spray segment. The plurality of spray orifices communicate between the inner surface and the outer surface and are configured to spray jets of fluid from the fluid lumen into an intraluminal space. The plurality of spray orifices each include an orifice path within the body wall defining an orifice path orientation relative to the longitudinal axis, the orifice path orientation including a radially advancing component and a circumferentially advancing component. The plurality of spray orifices further define a torque inducing spray jet pattern based at least in part on the radially advancing component and the circumferentially advancing component, whereby a back pressure of spray jets exiting the spray orifices induces a torque on the spray segment of the elongate catheter body.

BRIEF DESCRIPTION OF THE DRAWINGS

FIG. 4b is a partial view of the thrombolysis catheter of FIG. 4a;

FIG. 5 is a pictorial view of a portion of a thrombolysis mechanism similar to the mechanism of FIG. 1;

FIG. 6 is a pictorial view of a portion of a thrombolysis catheter, according to another embodiment;

FIG. 8 is a partially sectioned side diagrammatic view of a portion of the mechanism of FIG. 7, at another stage of an intravascular treatment procedure; and FIG. 9 is a partially sectioned side diagrammatic view of a portion of the mechanism of FIGS. 7 and 8, at yet another stage of an intravascular treatment procedure.

DETAILED DESCRIPTION

Figure 1:
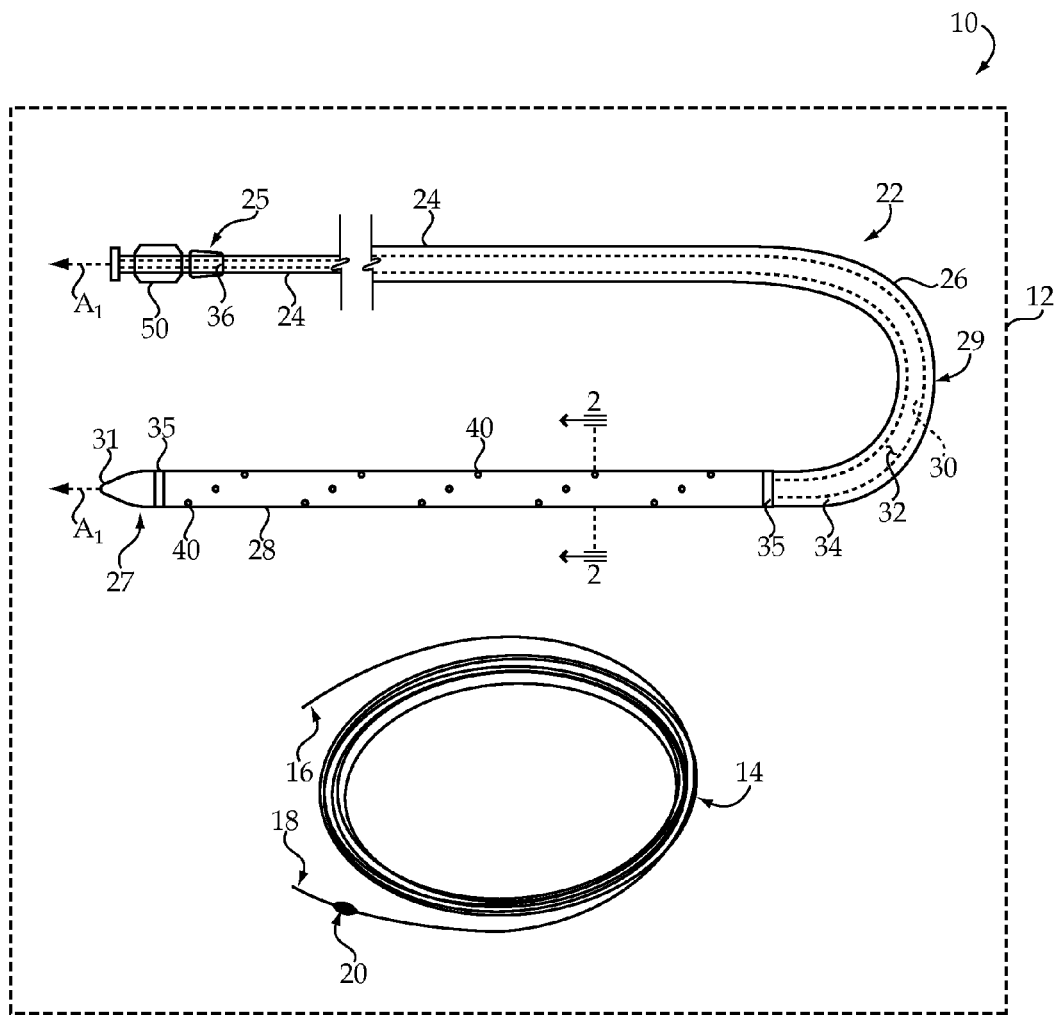
FIG. 1 is a side diagrammatic view of a packaged thrombolysis mechanism having a thrombolysis catheter, according to one embodiment.

Referring to FIG. 1, there is shown a thrombolysis mechanism 10 according to one embodiment. Mechanism 10 may include a thrombolysis catheter 22, and a wire guide 14, catheter 22 and wire guide 14 being positioned within a sterile package 12. Sterile package 12 may include a sealed, peel-open pouch in one embodiment. Other packaging features such as a tube protector coil or the like may be included but are not shown in FIG. 1. As will be further apparent from the following description, mechanism 10 may be uniquely configured for treating an intravascular site such as a thrombus in a patient.

Wire guide 14 may include a proximal wire guide tip 16, and a distal wire guide tip 18. An occlusion bulb 20 such as a hardened drop of solder or the like may be positioned just proximally of distal tip 18, for reasons further described herein.

Catheter 22 may include an elongate catheter body 24 having a proximal catheter end 25 and a distal catheter end 27 which includes a distal tip 31. A fitting such as a manifold 50 or the like may be coupled with proximal catheter end 25 and configured to supply a treatment fluid to elongate catheter body 24 as further described herein. Elongate catheter body 24 may further include a supply segment 26 and a spray segment 28, and may define a longitudinal axis $A_1$ extending through supply segment 26 and spray segment 28. Elongate catheter body 24 may further include an outer surface 29, and an inner surface 30 defining a longitudinally extending fluid lumen 32. A body wall 34 may extend between inner surface 30 and outer surface 29. Elongate catheter body 24 may further define a fluid supply port 36 located in supply segment 26 which fluidly connects with fluid lumen 32. As will be readily apparent to those skilled in the art, fluid supplied through manifold 50 from an extraluminal fluid supply may flow through port 36 into fluid lumen 32.

Elongate catheter body 24 may further define a plurality of spray orifices 40 formed in body wall 34 within spray segment 28 and fluidly communicating between inner surface 30 and outer surface 29. A set of radiopaque markers 35 may be positioned on or in elongate catheter body 24 within or adjacent to spray segment 28, for purposes well known in the art.

Figure 2:
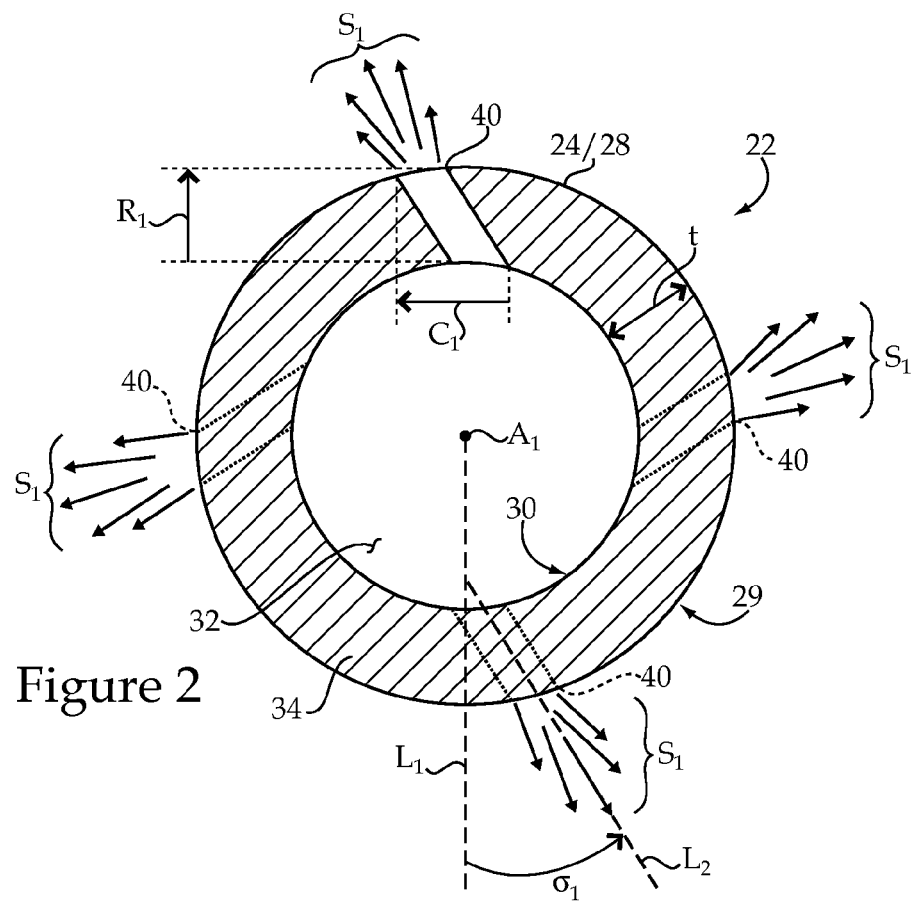
FIG. 2 is a sectioned view taken along line 2-2 of FIG. 1.

Referring also now to FIG. 2, there is shown a sectioned view along line 2-2 of FIG. 1. The section plane depicted in FIG. 2 intersects one of spray orifices 40, and other spray orifices 40 are shown in phantom. It may be noted that spray orifices 40 include a circumferential distribution within spray segment 28 about longitudinal axis $A_1$. It may further be noted that spray orifices 40 include an axial distribution within spray segment 28 relative to longitudinal axis $A_1$. In one embodiment, spray orifices 40 may be arranged in a helical distribution pattern defining a portion of a helix, a full helix, or multiple helices, about longitudinal axis $A_1$. In other embodiments, orifices 40 might be arranged in some other distribution pattern, for example, rather than a helical distribution pattern orifices 40 might be arranged in rows extending longitudinally along catheter body 24 at spaced apart axial locations relative to longitudinal axis $A_1$, but at uniform circumferential locations. The use of the helical distribution pattern, however, provides one practical implementation strategy.

Spray orifices 40 may be configured to spray jets of fluid, such as a treatment fluid supplied to fluid lumen 32 from an extraluminal fluid supply, into an intraluminal space such as an intraluminal treatment site within a vascular structure. Each of spray orifices 40 may have an orifice path within body wall 34 defining an orifice path orientation relative to longitudinal axis $A_1$. Orifices 40 may further define a torque inducing spray jet pattern whereby a back pressure of spray jets exiting spray orifices 40 induces a torque on spray segment 28 of elongate catheter body 24. Features of the orifice path orientation defined by spray orifices 40 facilitate inducing the described torque. The subject orifice path orientation may include a radially advancing component $R_1$ and a circumferentially advancing component $C_1$. The torque inducing spray jet pattern may be based at least in part on the radially advancing path component $R_1$ and the circumferentially advancing path component $C_1$.

As used herein, the term "radially advancing" should be understood to mean that the subject path component advances through body wall 34 in a radial direction which is perpendicular to longitudinal axis $A_1$. Radially advancing component $R_1$ may be equal to a thickness "t" of body wall 34. The term "circumferentially advancing" should be understood to mean that the subject path component advances circumferentially about outer surface 29. Circumferentially advancing component $C_1$ may be less than, equal to, or greater than, wall thickness t. Another way to understand these terms is that spray orifices 40 may each include a path which transitions from a radially inward location at inner surface 30 to a radially outward location at outer surface 29. Likewise, the path may transition from a first circumferential location about axis $A_1$ at inner surface 30 to a second circumferential location about axis $A_1$ at outer surface 29. In the embodiment depicted in FIG. 2, components $R_1$ and $C_1$ may be understood to lie in planes oriented perpendicular to longitudinal axis $A_1$. As further described herein, alternatives are contemplated wherein spray orifices include a radially advancing component, a circumferentially advancing component, and also an axially advancing component.

Also shown in FIG. 2 are sets of arrows each identified with reference letter $S_1$ which illustrate spray jets exiting spray orifices 40 according to an example torque inducing spray jet pattern defined by spray orifices 40. Fluid spraying out of each of spray orifices 40 may have a generally conical pattern, with each spray cone enlarging in a direction away from outer surface 29. Each of the spray cones, however, will define an average spray direction. In FIG. 2, a line $L_1$ is shown which intersects longitudinal axis $A_1$ and is oriented perpendicular thereto, passing through body wall 34. A second line $L_2$ is also shown which passes approximately through one of spray orifices 40. Line $L_2$ denotes an average spray direction defined by the corresponding conical spray jet, represented by the corresponding set of arrows $S_1$. It may be noted that an angle $\theta_1$ is defined by lines $L_1$ and $L_2$. In the illustrated embodiment, angle $\theta_1$ lies in the plane of the page, however, in other embodiments an angle defined in a similar manner for spray orifices having an axially advancing component would lie in a different plane. In one embodiment, angle $\theta_1$ may include an angle of about 45°. Spray orifices 40 may each include a circular cross section, and the associated average spray direction may be colinear with a center axis of the respective spray orifice. In other embodiments, a different cross sectional shape than a circular shape and/or even a non-uniform cross sectional shape varying between inner surface 29 and outer surface 30 might be used to impart a non-conical spray jet shape and/or an average spray direction not colinear with the orifice center axis.

Turning now to FIG. 5, there is shown a pictorial view of catheter 22 as it might appear with wire guide 14 positioned therein such that occlusion bulb 20 blocks an opening 33 in distal tip 31. In the configuration shown, fluid supplied to fluid lumen 32 may be blocked from passing out of distal tip 31, and instead pass out of spray orifices 40. The embodiment shown in FIG. 5 may thus be understood as a configuration suited for over-the-wire positioning and use of catheter 22. In other embodiments, catheter 22 might be configured as a rapid exchange catheter, wherein fluid lumen 32 is blocked proximally of distal tip 31 and wire guide 14 is passed through distal tip 31 or a portion thereof without entering fluid lumen 32.

Spray jets exiting spray orifices 40 may spray outwardly at an exit pressure into an intraluminal space. In FIG. 5, a set of arrows E are shown which depict vectors associated with an exit pressure of spray jets exiting spray orifices 40. Also shown in FIG. 5 are another set of arrows oriented in opposition to arrows E which depict vectors associated with a back pressure of spray jets exiting spray orifices 40. The back pressure represented by vector arrows B will tend to exert a force on elongate catheter body 24 which imparts a tendency to elongate catheter body 24, and in particular spray segment 28, to rotate. Each of vector arrows B represents an approximately linear force. Since a plurality of spray orifices 40 are used, and are positioned and oriented in elongate catheter body 24 as described herein, the linear forces may produce a net rotational force or torque, shown via arrow $T_1$ about longitudinal axis $A_1$. As further described herein, inducing a torque on elongate catheter body 24 can be advantageously used to change an impingement pattern of treatment fluid exiting spray orifices 40 on material within an intraluminal treatment site such as an intravascular site. Additionally, rotational motion of elongate catheter body 24, and in particular spray segment 28, can cause elongate catheter body 24 to contact material within an intravascular site such as thrombus material. Contact between elongate catheter body 24 and thrombus material can dislodge material of a thrombus, deform material of a thrombus, and/or otherwise assist in facilitating access of the subject treatment fluid to thrombus material.

Figure 3:
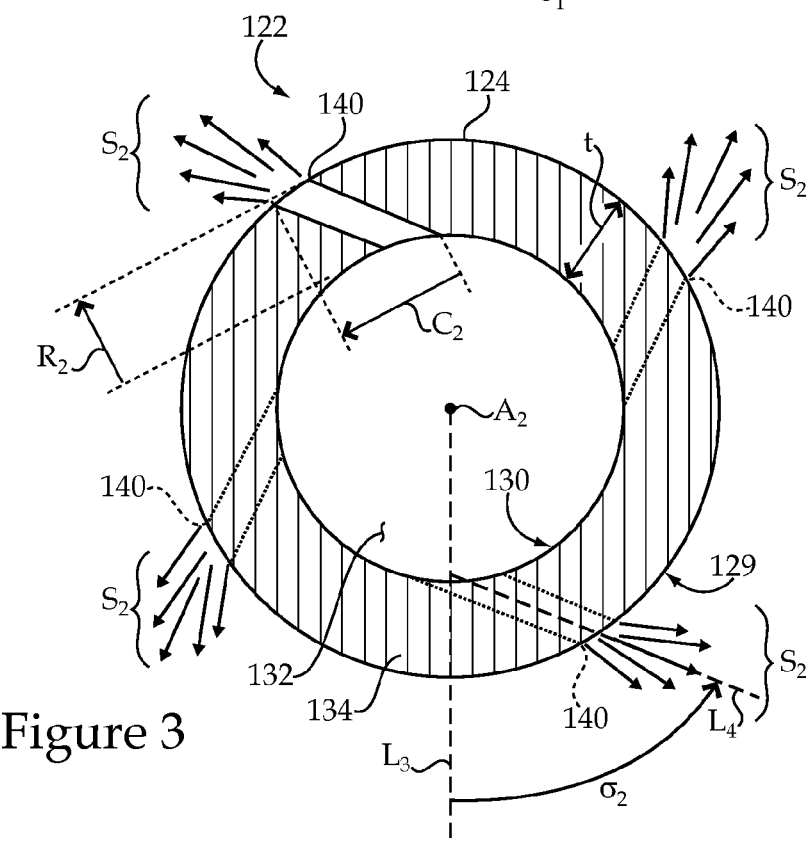
FIG. 3 is a sectioned view through a thrombolysis catheter, according to one embodiment.

Turning now to FIG. 3, there is shown a thrombolysis catheter 122 in a section plane similar to that of FIG. 2. Catheter 122 is similar to catheter 22, but includes several differences. Catheter 122 includes an elongate catheter body 124 having an outer surface 129, and an inner surface 130 defining a fluid lumen 132. A body wall 134 extends between inner surface 130 and outer surface 129. A plurality of spray orifices 140 are formed in body wall 134 and communicate between inner surface 130 and outer surface 129 to enable spraying jets of treatment fluid from fluid lumen 132 into an intraluminal space. Body wall 134 may include a wall thickness t which is the same as the wall thickness of body wall 34 of catheter 22. Spray orifices 140 may each include an orifice path within body wall 134 defining an orifice path orientation relative to a longitudinal axis $A_2$. Spray orifices 140 may include an axial distribution and a circumferential distribution within elongate catheter body 124. Similar to catheter 22, spray orifices 140 may include a helical distribution pattern.

Spray orifices 140 may each further include an orifice orientation defining a torque inducing spray jet pattern, based at least in part on a radially advancing component $R_2$ and a circumferentially advancing component $C_2$. A back pressure of spray jets exiting spray orifices 140 may induce a torque on elongate catheter body 124. In FIG. 3, a set of arrows $S_2$ is shown associated with each of spray orifices 140 and illustrates spray jets associated therewith. An average direction of the spray jets $S_2$ exiting spray orifices 140 is relatively closer to being tangential relative to outer surface 129 than that of spray jets $S_1$ relative to outer surface 29 as shown in FIG. 2.

The different spray jet pattern defined by spray orifices 140 of catheter 122 in comparison to spray orifices 40 of catheter 22 results at least in part from the different orifice path orientation associated with spray orifices 140 than that associated with spray orifices 40 of catheter 22. Radially advancing component $R_2$ may be substantially identical to radially advancing path component $R_1$. Circumferentially advancing component $C_2$, however, may be relatively greater than circumferentially advancing component $C_1$. In the example embodiment shown in FIG. 3, it may be assumed that spray orifices 140 have a similar cross sectional shape and cross sectional area to spray orifices 40. Since spray orifices 140 include an orientation defining a relatively large circumferentially advancing component, however, spray jets $S_2$ may induce a relatively greater torque on elongate catheter body 124 at a given exit pressure.

Also shown in FIG. 3 is a line $L_3$ which is in the plane of the page, intersects axis $A_2$, and is oriented perpendicular to axis $A_2$. Another line $L_4$ intersects line $L_3$ and is defined by one of spray orifices 140 in a manner analogous to that discussed with regard to catheter 22. Line $L_3$ and line $L_4$ define an angle $\theta_2$, which is relatively greater than angle $\theta_1$ associated with the FIG. 2 embodiment, and which may be equal to about 60°.

Figure 4A:
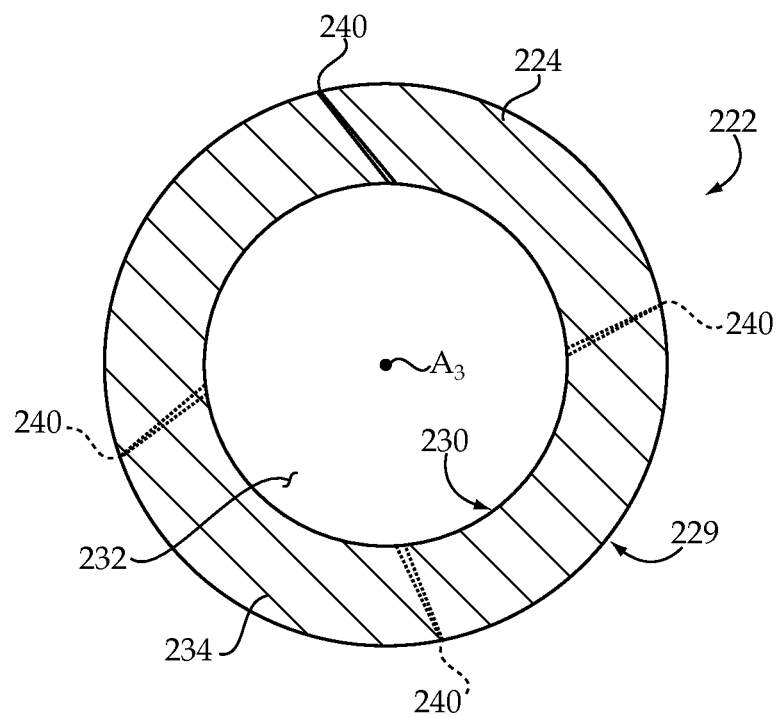
FIG. 4a is a sectioned view through a thrombolysis catheter, according to another embodiment.

Referring now to FIG. 4a, there is shown a thrombolysis catheter 222 according to yet another embodiment. Catheter 222 may include an elongate catheter body 224 having an outer surface 229, and an inner surface 230, defining a fluid lumen 232. A plurality of spray orifices 240 may be formed in a body wall 234 which extends between inner surface 230 and outer surface 229. The previously described embodiments may include normally open spray orifices. In contrast, spray orifices 240 may include normally closed or normally partially closed spray orifices. In particular, spray orifices 240 may include a rest configuration which corresponds to a zero or relatively small cross-sectional flow area, and an open configuration which corresponds to a relatively greater cross-sectional flow area. Each of spray orifices 240 may be configured to switch from the rest configuration to the open configuration in response to a pressure of fluid within fluid lumen 232.

Figure 4B:
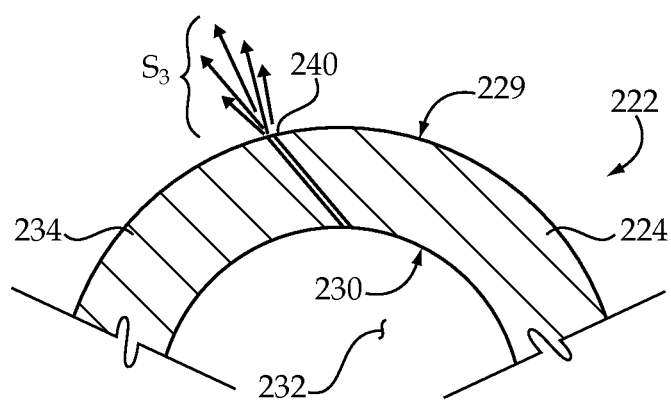

Pressurization of fluid in fluid lumen 232 may cause material of elongate catheter body 224 to deform and thereby open spray orifices 240. Referring also to FIG. 4b, there is shown a portion of elongate catheter body 224 where one of spray orifices 240 has been switched from its rest configuration, approximately as shown in FIG. 4a, to an open configuration. A spray jet $S_3$ is shown exiting the subject spray orifice 240. When treatment fluid is present in fluid lumen 232 at a relatively low pressure, spray orifices 240 may remain in their rest configuration, closed or restricted. Spray orifices 140 may remain in a rest configuration until a pressure of treatment fluid in fluid lumen 232 more or less equalizes along the entire spray length of elongate catheter body 224. Once pressure equalizes, and exceeds a threshold necessary to deform material of elongate catheter body 224 in the vicinity of spray orifices 240, spray jets $S_3$ may spray outwardly from outer surface 229.

In one embodiment, spray orifices 240 may include uniform orientations and configurations such as shape, length, cross sectional flow area. In other embodiments, spray orifices 240 might include progressively larger spray orifices in a proximal to distal direction along a spray length of elongate catheter body 224. These factors might also be varied in the other embodiments described herein. In one embodiment, a pressure of treatment fluid might be supplied to fluid lumen 232 at a more or less constant pressure, and spray orifices 240 could open in response to the pressure, close as the pressure is reduced, then open once again as the pressure returns to above a threshold. Supply pressure of treatment fluid could also be pulsed externally of the patient, in any of the embodiments described herein.

Turning now to FIG. 6, there is shown a catheter 322 according to yet another embodiment. Catheter 322 may include a thrombolysis catheter having an elongate catheter body 324 defining a longitudinal axis $A_4$. Elongate catheter body 324 may include an outer surface 329, an inner surface 330, and a body wall 334 extending between inner surface 330 and outer surface 329. Inner surface 330 may define a longitudinally extending fluid lumen 332. A plurality of spray orifices 340 may be formed in body wall 334, and communicate between inner surface 330 and outer surface 329 such that jets of treatment fluid (not shown) may be sprayed from outer surface 329 into an intraluminal space. Similar to embodiments described above, each of spray orifices 340 may include an orifice path within body wall 334 defining an orifice path orientation relative to longitudinal axis $A_4$. The subject orifice path orientation may include a radially advancing component and a circumferentially advancing component, defining a torque inducing spray jet pattern.

In contrast to the embodiments described above, the orifice path orientation in catheter 322 may further include an axially advancing component. It may be noted that spray orifices 340 open at inner surface 330 at axial locations and open at outer surface 329 at different axial locations. The orifice path associated with each of orifices 340 may thus advance in catheter body 324 relative to longitudinal axis $A_4$.

It may thus be appreciated that a variety of different orifice path orientations and orifice shapes are contemplated in the context of the present disclosure. Also shown in FIG. 6 are a set of arrows E which indicate vectors associated with an exit pressure of spray jets exiting spray orifices 340. Another set of arrows B, approximately oriented in opposition to arrows E, illustrate vectors associated with a back pressure of the subject spray jets. Each of vector arrows B denotes a linear force. Rather than a linear force in a plane perpendicular to longitudinal axis $A_4$, vector arrows B define orientations which are out of such a plane. In the illustrated embodiment, the linear forces illustrated via vector arrows B may tend to sum to a force on catheter body 24 which includes both a linear, axial component $T_4$ and a torque component $T_3$. In the FIG. 6 embodiment, spray orifices 340 axially advance in a proximal to distal direction. In other embodiments, spray orifices 340 might axially advance in a distal to proximal direction.

As described above, embodiments contemplated within the context of the present disclosure include catheters wherein spray jets of fluid induce a torque on an elongate catheter body. Embodiments are contemplated (not shown) in which a bearing is positioned in the elongate catheter body such that a distal segment which includes a spray segment can freely rotate relative to a supply segment in response to induced torque. In such an embodiment, the point of rotation may be within a patient during use. As further described herein, rotation of the elongate catheter body may also take place by twisting the elongate catheter body in response to the induced torque.

Some resistance to twisting may be associated with any catheter mechanism. Accordingly, when an elongate catheter body is twisted as described herein, the twisting may occur against a counter-torque which is based on various factors associated with a given system. Factors affecting the relative difficulty in twisting may include factors inherent to a particular design such as the material composition of the catheter, a length of the catheter, a diameter of the catheter, a thickness of the body wall between the inner surface and outer surface, whether normally open or normally closed spray orifices are used, and shape, length, and cross-sectional flow area of the spray orifices. These and other factors may define a twisting resistance torque coefficient associated with an elongate catheter body such as those described herein. Other factors which are not inherent to a particular catheter may also affect the relative difficulty in twisting in vivo. These may include, for instance, the number and sharpness of turns negotiated by the catheter within a patient's body, the geometry of the treatment site, proximity to or contact between the outer surface of the catheter and material within the treatment site, and supply pressure or supply pressure dynamics. Catheters according to the present disclosure may nevertheless be configured on the basis of the inherent factors defining the twisting resistance torque coefficient in at least certain instances.

In one embodiment, the orifice path orientation defined by spray orifices 40, 140, 240, 340, may be linked with the twisting resistance torque coefficient. This means that an orientation of the subject spray orifices within the corresponding elongate catheter body 24, 124, 224, 324, may be based at least in part on the relative difficulty of twisting the subject elongate catheter body within a patient. An elongate catheter body may be relatively more difficult to twist because it is formed of relatively stiffer material, has a relatively thick body wall, and is relatively short, for example. Such a catheter may be understood to define a relatively higher twisting resistance torque coefficient. Orifice path orientation of the spray orifices in such a catheter may be tailored to enable inducing a relatively higher torque via back pressure of spray jets exiting the subject elongate catheter body. For an elongate catheter body which is relatively easier to twist, the orifice path orientation might be tailored to induce a relatively lesser torque.

It may be recalled that spray orifices 40 of catheter 22 may define a relatively less tangential spray jet pattern, whereas spray orifices 140 of FIG. 3 may define a relatively more tangential spray jet pattern. As described above, various factors may bear on the actual magnitude of torque induced on an elongate catheter body by spraying jets of treatment fluid. Holding all factors equal but for orifice path orientation, spray jets $S_2$ in the embodiment of FIG. 3 could be expected to induce a relatively greater torque on elongate catheter body 124 than the torque induced by spray jets $S_1$ on elongate catheter body 24.

As alluded to above, spray orifices according to the present disclosure may also include a variety of orifice shapes. Spray orifices having a circular cross section may be used, as well as spray orifices having a triangular cross section or some other shape. Normally closed spray orifices or normally open spray orifices, or a combination of normally open and normally closed spray orifices could be used. In addition to orifice path orientation as described above, spray orifices according to the present disclosure may also include an orifice shape profile linked with the corresponding twisting resistance torque coefficient. For instance, spray orifices having a uniform circular cross section between the corresponding inner surface and outer surface may be understood to have a first orifice shape profile associated with a first torque magnitude for a given spray pressure. Spray orifices having a uniform triangular cross section between the corresponding inner surface and outer surface may be understood to have a second orifice shape profile associated with a different torque magnitude at a given supply pressure. The orifice shape profiles may be based at least in part on, and thus linked with, a twisting resistance torque coefficient for the corresponding catheter. Still other characteristics of spray orifice shape and their relative effectiveness in twisting the associated catheter may be empirically determined.

INDUSTRIAL APPLICABILITY

Figure 7:
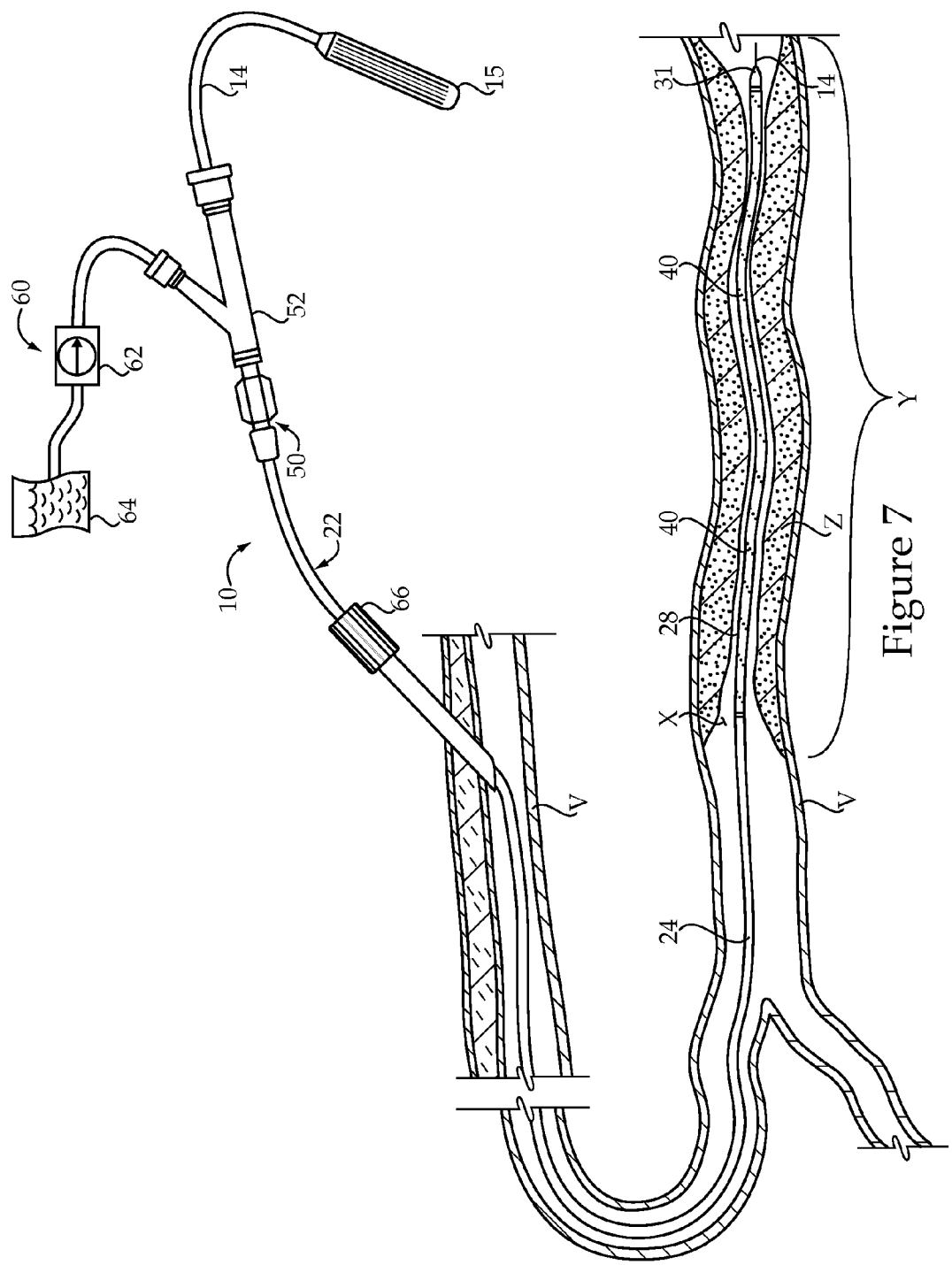
FIG. 7 is a partially sectioned side diagrammatic view of a thrombolysis mechanism, at one stage of an intravascular treatment procedure.

Referring to FIG. 7, there is shown a catheter mechanism 10 similar to that of FIG. 1. It may be recalled that catheter mechanism 10 may include a manifold 50, for example insert molded or otherwise affixed to elongate catheter body 24. Mechanism 10 is shown as it might appear having been placed by way of percutaneous access within a vascular structure V of a patient. Wire guide 14 is shown equipped with a handle 15, and has been used to reach an intravascular treatment site Y within vascular structure V, and thenceforth used to guide elongate catheter body 24 to intravascular treatment site Y by way of over-the-wire placement. Elongate catheter body 24 has been positioned such that spray orifices 40 within spray segment 24 are located within an intraluminal space X within intravascular treatment site Y. Wire guide 14 protrudes distally out of distal tip 31, and blocks fluid lumen 32 at or near distal tip 31 with occlusion bulb 20. In the illustrated embodiment, an intravascular material Z such a thrombus is within intravascular treatment site Y. An access device such as an introducer sheath 66 penetrates the patient's skin and enables percutaneous access to vascular structure V. A fluid supply 60 is shown connected with manifold 50 by way of a Y-fitting 52. Fluid supply 60 may include a fluid reservoir 64 and an infusion pump 62 in one embodiment, such that fluid may be pumped from reservoir 64 through elongate catheter body 24 and thenceforth sprayed out of spray orifices 40 into intraluminal space X.

Referring also to FIG. 8, there is shown a close-up view of elongate catheter body 24, positioned within intravascular treatment site Y. Elongate catheter body 24 is shown as it might appear upon commencing spraying jets $S_1$ of treatment fluid out of spray orifices 40. A torque induced by way of a back pressure of spray jets $S_1$ is depicted with arrow $T_1$. It may be noted that spray jets $S_1$ impinge upon material Z within intravascular site Y in an impingement pattern. The impingement pattern of spray jets $S_1$ on material Z may be changed in response to induced torque $T_1$. In one embodiment, spray orifices 40 may be repositioned relative to material Z by rotating or otherwise repositioning spray segment 28 within intravascular treatment site Y in response to torque $T_1$. In FIG. 8, a second arrow $T_2$ illustrates a counter torque associated with twisting resistance of elongate catheter body 24. Accordingly, torque $T_2$ acts in opposition to torque $T_1$.

Referring also to FIG. 9, there is shown elongate catheter body 24 as it might appear having been twisted in response to the induced torque on spray segment 28. It may be noted that an impingement pattern of spray jets $S_1$ on material Z has changed from the impingement pattern in FIG. 8. It may also be noted that spray segment 28 has not only rotated relative to material Z, but has also come into contact with material Z in a zone denoted via reference letter Q. Changing an impingement pattern may thus further include dislodging or deforming intravascular material Z at least in part by contacting intravascular material Z with elongate catheter body 24 in response to the induced torque. It is believed that bits of material Z may be broken off, or that material Z in zone Q may have its shape deformed to expose material to the treatment fluid which was previously covered by other material. In general, it is expected that rotating and in some instances changing the configuration or orientation of spray segment 28 via torque $T_1$ can hasten lysing of material Z in a variety of ways. This can include breaking up material Z, deforming material Z to expose previously covered surfaces to the treatment fluid, and also changing which parts of material Z are directly impinged upon by treatment fluid of spray jets $S_1$. Pressure of spray jets $S_1$ may also assist in mechanically breaking up material Z.

A plurality of twist points P of elongate catheter body 24 are also depicted in FIG. 9. In some embodiments, spray segment 28 may experience one or more full rotations in response to torque $T_1$. In other instances, spray segment 28 might experience less than one full rotation about longitudinal axis $A_1$. It is nevertheless contemplated that essentially any induced rotation of spray segment 28 may be sufficient to change the impingement pattern of spray jets $S_1$ on material Z. It may further be noted from FIG. 9 that counter torque $T_2$ is represented with an arrow approximately the same size as induced torque $T_1$. As elongate catheter body 24 is twisted, the counter torque $T_2$ may increase based on increasing tension and/or compression of material in elongate catheter body 24.

Transitioning from the catheter configuration and impingement pattern shown in FIG. 8 to the catheter configuration and impingement pattern shown in FIG. 9 may be achieved by pulsing an exit pressure of the treatment fluid from the spray orifices 40. In particular, jets $S_1$ might be generated to induce torque $T_1$ on spray segment 28, then spraying stopped, and spray segment 28 allowed to counter-rotate via counter torque $T_2$. Spraying jets $S_1$ may then again be generated, and spray segment 28 rotated in response to an induced torque, and again allowed to counter rotate to a relaxed state. This general strategy of pulsing exit pressure of fluid from spray orifices 40, and twisting elongate catheter body 24 via a back pressure of jets $S_1$ pulsed in accordance with the exit pressure, may result in inducing rotation pulses of elongate catheter body 24. As described herein, elongate catheter body 24 may twist in response to induced torque with each of the rotation pulses, and then untwist in response to counter-torque. In one embodiment, pulsing of spray jets $S_1$ might be achieved by pulsing a supply pressure of treatment fluid to catheter 22 by way of pump 62. In another embodiment, pump 62 or another supply mechanism might supply treatment fluid to catheter 22 at a relatively uniform pressure, and normally closed spray orifices might be used to provide pulsed spray jets. All the while, material Z may be dissolved by way of the treatment fluid. When a course of treatment has been concluded, elongate catheter body 24 and wire guide 14 may be withdrawn through introducer sheath 66 in a conventional manner.

As discussed above, a variety of factors may be relevant to obtaining desired spray characteristics and twisting/rotation characteristics of a thrombolysis catheter according to the present disclosure. Factors such as spray orifice shape profile, orifice path orientation, wall thickness, length of spray segment, length of supply segment, and material from which a catheter is formed may all be relevant to achieving these goals. Moreover, manipulation by a clinician of the catheter from a location outside of the patient can also affect the behavior of a thrombolysis catheter as disclosed and used herein. In one practical implementation strategy, each of the elongate catheter bodies 24, 124, 224, 324, may be formed from an extruded material such as nylon or polytetrafluoroethylene. The extrusion can be coupled with manifold 50 by any suitable mechanism. Spray orifices 40, 140, 240, 340 may be formed by any suitable technique, such as the use of a piercing needle or the like. In one particular embodiment, elongate catheter bodies according to the present disclosure might include an outer diameter in the range of three French (FR) to six French (FR). A length of spray segment 28, for example between radiopaque markers/bands 35, might be between 5 centimeters and 60 centimeters. A total axial length of between supply port 36 and a terminal end of distal tip 31 in catheter 22, may be between 40 centimeters and 160 centimeters. In one further example, a catheter might include an outer diameter of 5 FR, a total length of 150 centimeters, and a spray segment length of 30 centimeters.

Duration of a percutaneous treatment procedure such as treatment of a thrombus as depicted in FIGS. 7-9 may last anywhere from less than one hour to several hours. Inducing rotation pulses by generating spray jets $S_1$, for example, might take place essentially continuously throughout this time period. For instance, spray jets might be generated every few seconds or every few minutes. For arterial infusion, treatment fluid might be infused at a rate between 5 cubic centimeters per hour and 20 cubic centimeters per hour, whereas venous infusion might occur at a rate between 20 cubic centimeters per hour and 80 cubic centimeters per hour.

The foregoing embodiments set forth practical implementation strategies, however, the present disclosure is not thereby limited and relatively thicker or thinner catheters, relatively longer or shorter catheters, and different treatment durations and infusion rates might be used. Each of the contemplated embodiments, however, by virtue of the unique spray orifice configuration disclosed herein is considered to provide advantageous catheter behavior and thrombus treatment without the need for motors, ultrasonic energy, or external manipulation, and without sacrificing tensile strength and/or pushability.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A method of treating an intravascular site in a patient with a thrombolysis catheter that includes an elongate catheter body having a supply segment and a spray segment, and defining a longitudinal axis extending through the supply segment and the spray segment, the elongate catheter body further having an outer surface, an inner surface defining a longitudinally extending fluid lumen, and a body wall extending between the inner surface and the outer surface; the elongate catheter body further defining a fluid supply port located in the supply segment and connecting with the fluid lumen, and a plurality of spray orifices formed in the body wall within the spray segment, the plurality of spray orifices communicating between the inner surface and the outer surface and being configured to spray jets of fluid from the fluid lumen into an intraluminal space; the plurality of spray orifices each having an orifice path within the body wall defining an orifice path orientation relative to the longitudinal axis, the orifice path orientation including a radially advancing component and a circumferentially advancing component; and the plurality of spray orifices further defining a torque inducing spray jet pattern based on the radially advancing component and the circumferentially advancing component, whereby a back pressure of spray jets exiting the spray orifices induces a torque about the longitudinal axis on the spray segment of the elongate catheter body, and the method comprising the steps of:
   supplying a treatment fluid to the fluid lumen of the elongate catheter body, positioned within an intravascular site;
   spraying jets of treatment fluid out of the spray orifices formed in the elongate catheter body;
   inducing a torque on the elongate catheter body about the longitudinal axis by way of a back pressure of the jets; and
   changing an impingement pattern of the treatment fluid on material within the intravascular site in response to the torque.

2. The method of claim 1 wherein the step of changing an impingement pattern further includes repositioning the spray orifices relative to an intravascular material.

3. The method of claim 2 wherein the step of changing an impingement pattern further includes dislodging or deforming intravascular material at least in part by contacting the intravascular material with the elongate catheter body in response to the torque.

4. The method of claim 2 wherein the step of spraying further includes spraying the jets of treatment fluid in the torque inducing spray jet pattern defined by an orientation of the spray orifices within the body wall of the elongate catheter body.

5. The method of claim 4 wherein the step of spraying further includes pulsing an exit pressure of the treatment fluid from the spray orifices, and wherein the step of inducing a torque further includes pulsing the back pressure in accordance with the exit pressure.

6. The method of claim 5 wherein the step of changing an impingement pattern further includes a step of inducing rotation pulses of the elongate catheter body in response to pulsing the back pressure.

7. The method of claim 6 wherein the step of inducing rotation pulses further includes a step of twisting the elongate catheter body with each of the rotation pulses, the method further including a step of untwisting the elongate catheter body in response to a counter-torque induced by twisting the elongate catheter body.

8. The method of claim 4 wherein the step of changing an impingement pattern further includes changing an impingement pattern of the treatment fluid on a thrombus, the method further including a step of dissolving the thrombus with the treatment fluid.

9. The method of claim 8 further comprising the steps of percutaneously accessing the intravascular site, and pressurizing the treatment fluid within the fluid lumen at least in part by pressurizing the treatment fluid outside of the patient.

10. A thrombolysis catheter comprising:
    an elongate catheter body having a supply segment and a spray segment, and defining a longitudinal axis extending through the supply segment and the spray segment, the elongate catheter body further having an outer surface, an inner surface defining a longitudinally extending fluid lumen, and a body wall extending between the inner surface and the outer surface;
    the elongate catheter body further defining a fluid supply port located in the supply segment and connecting with the fluid lumen, and a plurality of spray orifices formed in the body wall within the spray segment, the plurality of spray orifices communicating between the inner surface and the outer surface and being configured to spray jets of fluid from the fluid lumen into an intraluminal space; and
    the plurality of spray orifices each having an orifice path within the body wall defining an orifice path orientation relative to the longitudinal axis, the orifice path orientation including a radially advancing component and a circumferentially advancing component; and
    the plurality of spray orifices further defining a torque inducing spray jet pattern based on the radially advancing component and the circumferentially advancing component, whereby a back pressure of spray jets exiting the spray orifices induces a torque about the longitudinal axis on the spray segment of the elongate catheter body.

11. The thrombolysis catheter of claim 10 wherein each of the plurality of spray orifices includes a spray orifice having a rest configuration and an open configuration, each of the spray orifices being configured to switch from the rest configuration to the open configuration in response to a pressure of fluid within the fluid lumen.

12. The thrombolysis catheter of claim 10 wherein the plurality of spray orifices include each of an axial distribution and a circumferential distribution, within the spray segment.

13. The thrombolysis catheter of claim 12 wherein the plurality of spray orifices include a helical distribution pattern.

14. The thrombolysis catheter of claim 12 wherein the elongate catheter body defines a twisting resistance torque coefficient, and wherein the orifice path orientation is linked with the twisting resistance torque coefficient.

15. The thrombolysis catheter of claim 14 wherein each of the plurality of spray orifices further includes an orifice shape profile linked with the twisting resistance torque coefficient.

* * * * *